United States Patent

Barreras

[11] Patent Number: 4,594,565
[45] Date of Patent: Jun. 10, 1986

[54] CLOCK OSCILLATOR FOR A CARDIAC PACER HAVING FREQUENCY COMPENSATION FOR TEMPERATURE AND VOLTAGE FLUCTUATIONS

[75] Inventor: Francisco J. Barreras, Miami, Fla.

[73] Assignee: Cordis Corporation, Miami, Fla.

[21] Appl. No.: 646,222

[22] Filed: Aug. 30, 1984

[51] Int. Cl.[4] .......................... H03K 3/57; H03L 1/02
[52] U.S. Cl. ................................ 331/108 A; 331/111; 331/176; 128/422
[58] Field of Search ................ 331/108 A, 111, 176; 128/419 PG, 422

[56] References Cited

U.S. PATENT DOCUMENTS

| | | | |
|---|---|---|---|
| 3,995,232 | 11/1976 | Laugesen | 331/111 |
| 4,365,212 | 12/1982 | Gentile et al. | 331/111 |
| 4,370,628 | 1/1983 | Henderson et al. | 331/111 |
| 4,453,834 | 6/1984 | Suzuki et al. | 331/111 X |

Primary Examiner—Eugene R. LaRoche
Assistant Examiner—D. C. Mis
Attorney, Agent, or Firm—Lockwood, Alex, FitzGibbon & Cummings

[57] ABSTRACT

A temperature and voltage stable clock circuit for use in implantable cardiac pacers employs CMOS devices to minimize current drain. The circuit includes a timing capacitor which is alternately charged to and discharged between two established threshold voltages during respective charge and discharge cycles, the periods of which determine the clock frequency. To render the frequency of the clock circuit independent of changes in capacitor charge and discharge currents brought about by changes in temperature, the threshold voltage is increased with temperature so that the charge and discharge cycles remain constant. To render the frequency of the clock circuit independent of changes in the power supply voltage, a Wilson current source is used to maintain a constant charge and discharge current to the timing capacitor.

13 Claims, 5 Drawing Figures

CLOCK OSCILLATOR FOR A CARDIAC PACER HAVING FREQUENCY COMPENSATION FOR TEMPERATURE AND VOLTAGE FLUCTUATIONS

BACKGROUND OF THE INVENTION

The present invention is directed generally to cardiac pacers and more particularly to a voltage and temperature stable low-power clock circuit for use with implantable battery operated cardiac pacers.

In order to avoid the need for premature invasive battery replacement surgery, circuits intended for use in battery operated implantable cardiac pacers should preferably require minimal electrical power. Furthermore, such circuits should maintain desired operating characteristics despite changes in battery voltage and temperature. Specifically, in the case of pacer clock circuits, the clock frequency should be independent of operating temperature, in order that it can be accurately set while the device is at room temperature (23° C.) prior to implantation within a patient's body.

Clock circuits currently in use with battery operated implantable cardiac pacers are typically of the regenerative RC oscillator type, wherein a capacitor alternately charged and discharged through a resistor, determines clock frequency. Since the frequency determining components in such clock circuits are temperature sensitive, a change in ambient temperature alters the clock frequency unless suitable temperature compensation circuitry is provided. Furthermore, in such regenerative RC circuits, battery current is drawn during both the capacitor charge and discharge cycles, thereby imposing a relatively high power requirement.

Complementary-MOS (CMOS) circuitry is well suited for use in battery operated implantable cardiac pacers since such devices by their nature draw extremely little current while in operation. Consequently, a clock circuit intended for use in an implantable cardiac pacer can employ CMOS active devices to advantage to replace other more power consuming active devices. Since CMOS devices are relatively unaffected by variations in supply voltage, their use in battery-operated circuitry is particularly attractive where it is desired that circuit performance be maintained as the battery ages.

Accordingly, it is a general object of the present invention to provide a new and improved clock circuit for use in battery operated devices such as cardiac pacers.

It is a more specific object of the invention to provide a cardiac pacer clock circuit requiring minimal current during operation.

It is a more specific object of the invention to provide a clock circuit for use in cardiac pacers wherein the clock frequency remains constant over a range of ambient temperatures and supply voltages.

SUMMARY OF THE INVENTION

A clock circuit for use in a battery operated cardiac pacer or the like includes a timing capacitor, charge circuit means operable in response to an applied control signal for applying a charge current to the capacitor and discharge circuit means operable in response to an applied control signal for applying a discharge current to the capacitor. At least one of the circuit means produces a current which undesirably varies as a function of ambient temperature. First threshold means responsive to the voltage level across the timing capacitor produces a first control signal to inhibit the discharge circuit means and actuate the charge circuit means upon the capacitor voltage reaching a first threshold voltage, and second threshold means responsive to the voltage level across the timing capacitor produces a second control signal to inhibit the charge circuit means and actuate the discharge circuit means upon the capacitor voltage reaching a second threshold voltage. Temperature compensating means in circuit relationship with at least one of the threshold means vary the threshold voltage thereof in response to changes in temperature whereby the frequency of the charging cycle remains constant notwithstanding changes in ambient temperature.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
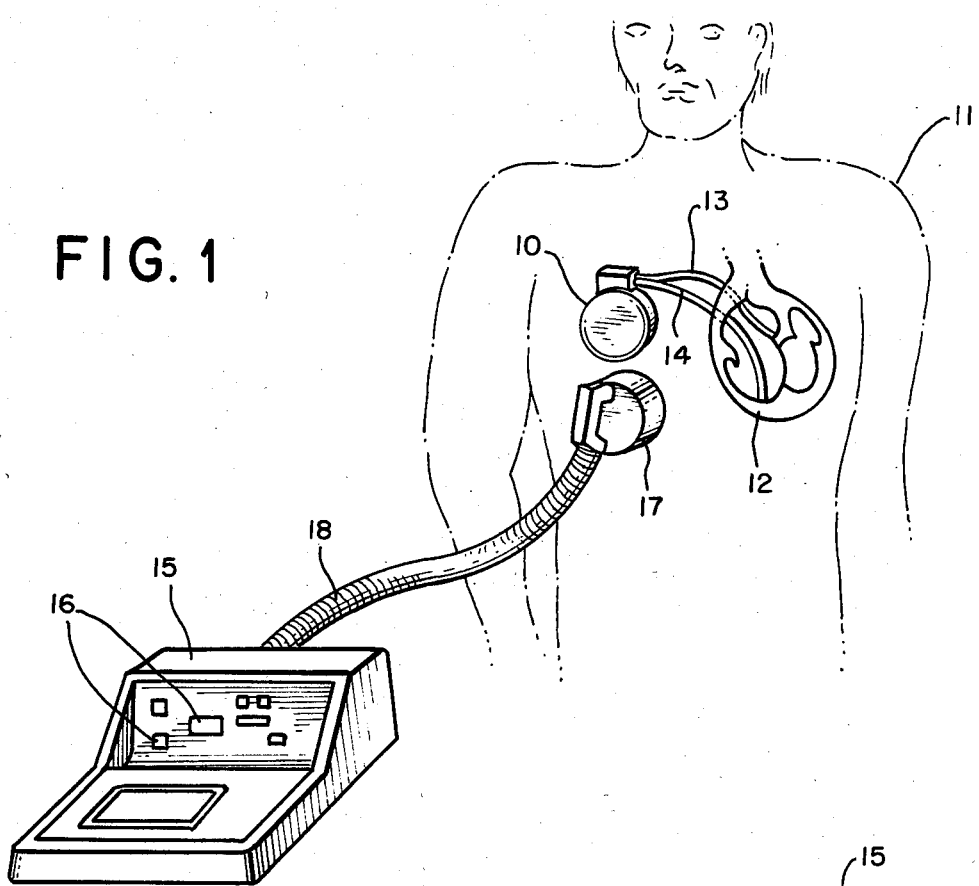
FIG. 1 is a perspective view of a battery powered implantable cardiac pacer system including a low power temperature and voltage stable clock circuit constructed in accordance with the invention.

Referring to the figures, and in particular to FIG. 1, a battery operated implantable programmable cardiac pacer 10 is shown implanted within a patient 11. The output of the pacer is connected to the patient's heart 12 (shown in cross section) by means of pacer leads 13 and 14, which may be conventional in design and construction. The pacer 10 is preferably formed as a self-contained and hermetically sealed device such that its operation is unaffected by exposure to body fluids.

Operation of the pacer can be modified as required by a specific application by means of a multiplex-type monitor and control programmer apparatus 15 external to the patient. The apparatus, which may also be conventional in design and construction, includes a number of user actuable controls 16 by which the user can selectively vary certain operating functions and parameters of the pacer. Communication between the control apparatus 15 and the pacer is provided by a magnetic or radio-frequency communication unit 17 positioned on the chest of the patient in close proximity to the implanted pacer. The transceiver transmits and receives telemetry data to and from the pacer in a manner well known to the art, and the resulting electrical signal is conveyed to and from the apparatus through a flexible electical cable 18.

Figure 2:
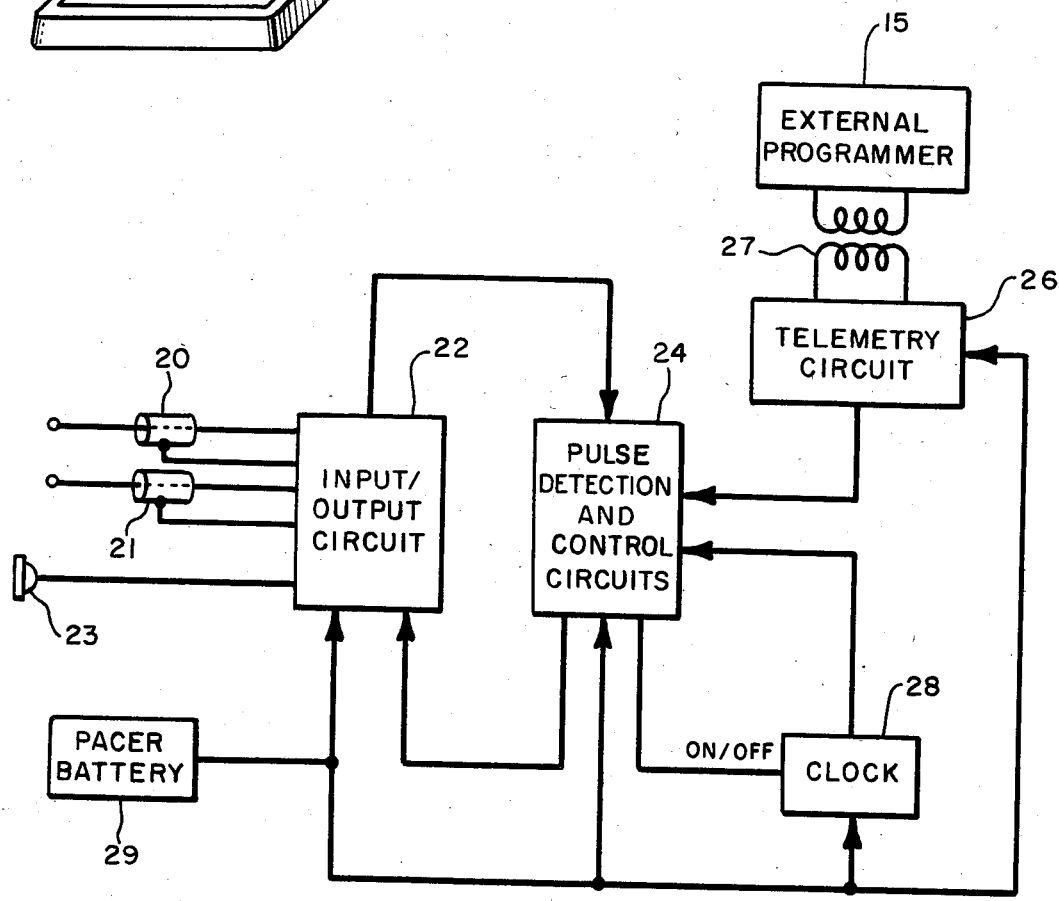
FIG. 2 is a functional block diagram showing the principal elements of the cardiac pacer system of FIG. 1.

Referring to FIG. 2, the implanted cardiac pacer 10 is seen to include an atrial terminal 20 for connection to the atrium of the heart, and a ventricular terminal 21 for connection to the ventricle of the heart. These terminals are each coaxial in construction, and are individually connected to an input/output circuit 22 wherein appropriate connections are established between the electrodes and the sensing and pacing circuitry of the pacer in accordance with a user-selected operating mode. An additional electrode 23, which may comprise the electrically conductive surface of the pacer housing, provides a reference for the atrial and ventricular terminals.

A pulse detection and control circuit 24 produces atrial and ventricular drive pulses for application to the input/output circuit 22 in response to R-wave and P-wave signals received from the atrial and ventricular terminals 20 and 21, respectively. These drive pulses cause generation of pacer output pulses of predetermined amplitude and duration on the atrial and ventricular terminals for application to respective chambers of the heart by pacer leads 13 and 14 (FIG. 1).

The operation of the pulse detection and control circuit 24 can be controlled from an external location by means of telemetry circuit 26. This circuit includes a pickup element 27 for receiving an appropriately coded magnetic or radio frequency control signal, and generates appropriate control signals for application to the pulse detection and control circuit 24 in response to coded instructions so received.

Referring further to FIG. 2, a clock circuit 28 constructed in accordance with the invention is provided within pacer 10 to supply clock pulses required for operation of pacer circuits 22, 24 and 26. The clock pulses thus supplied, which may in practice have a frequency range from 8 KHz to 320 KHz, are applied directly to pulse detection and control circuits 24. To turn the clock circuit on or off, an appropriate logic control signal, generated by control circuits 24, is applied to the clock through an ON/OFF line. A battery 29, of known construction, provides electrical power required for operation of the various pacer circuits.

Figure 3:
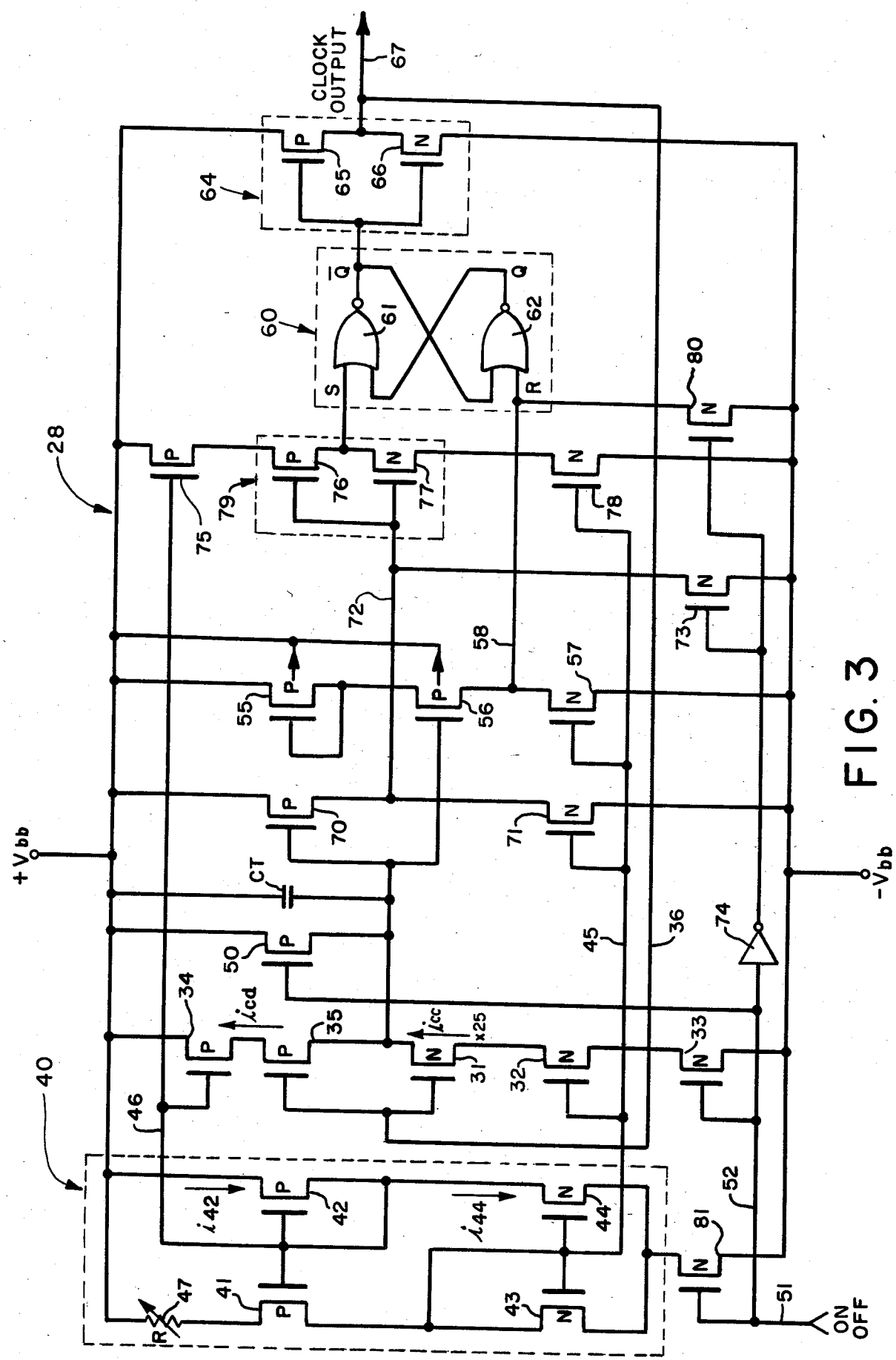
FIG. 3 is a simplified schematic diagram of the clock circuit included in the cardiac pacer.

Referring to FIG. 3, clock circuit 28 is seen to be of CMOS construction for minimal current drain. Within the clock circuit output pulses are generated by the alternate charging and discharging of a timing capacitor $C_t$. During the charging portion of each such timing cycle, current is supplied to the capacitor from system battery source $+V_{bb}$ by a charging circuit which includes three series-connected N-channel MOS transistors 31, 32 and 33. During the discharge portion of each timing cycle, current is drawn from the capacitor through a discharge circuit which includes two series-connected P-channel MOS transistors 34 and 35.

The charge and discharge circuits are alternately rendered operative by a control signal applied to transistors 31 and 35 on a control line 36. When this line is logic high, transistor 35 is biased off and transistor 31 is biased on, causing the capacitor to be charged through transistors 31, 32 and 33. When the line is logic-LOW, transistor 31 is inhibited and transistor 35 is enabled, causing the capacitor to discharge through transistors 34 and 35.

The magnitude of the charge current is controlled by two N-channel transistors 43 and 44, which are connected together with transistors 41 and 42 in a conventional manner between $+V_{bb}$ and $-V_{bb}$ to form a Wilson current source 40. This current source provides, in a manner well known to the art, a stable voltage-independent reference current level. This reference level, as it exists at transistors 43 and 44, is applied by conductor 45 to transistor 32, wherein it establishes the current level through the transistor, and hence the charging current applied to timing capacitor $C_t$. Similarly, the reference current level as it exists at transistors 41 and 42, is applied by a conductor 46 to transistor 34, wherein it establishes the current level through that device, and hence the discharge current level of the timing capacitor. In accordance with conventional practice, a resistor 47 is provided in the Wilson current source circuit 40 to permit adjustment of the reference current level.

In operation, the charge and discharge currents are alternately applied during respective charge and discharge periods, during which periods such currents remain substantially constant at a level proportional to the reference level provided by the Wilson current source. It is a feature of this invention that the charge and discharge currents are independently set, and need not be equal to each other.

A alternate discharge path for timing capacitor $C_t$ is provided by a P-channel transistor 50, the principal electrodes of which are connected across the capacitor. When the oscillator circuit is turned off by means of a logic-LOW signal applied to ON/OFF terminal 51 and associated control line 52, transistor 50 is biased on, resulting in discharge of the capacitor. At the same time transistor 33 is biased off. This assures that the capacitor $C_t$ remains discharged while the clock circuit is switched off.

To provide control signals for controlling the timing capacitor charge and discharge circuit, clock circuit 28 is provided a with first threshold detection circuit, in the form of two P-channel transistors 55 and 56. The source of transistor 55 is connected to $+V_{bb}$ and the gate and drain are connected to the source of transistor 56. The gate of transistor 56 is connected to one terminal of timing capacitor $C_t$. With this arrangement, when the voltage at the capacitor terminal reaches the threshold level established by transistors 55 and 56, the transistors are biased on. An N-channel transistor 57, having principal electrodes connected in series with transistors 55 and 56, and a control electrode connected to reference line 45, serves as a pull down active load for transistors 55 and 56. When biased on, the transistors 55 and 56 will overcome transistor 57 thereby biasing line 58 HIGH.

Upon the threshold level being reached, transistors 55 and 56 produce a control signal, which is applied on a control line 58 to the RESET terminal of an RS flip-flop 60. In this embodiment, the RS flip-flop 60 comprises a pair of NOR gates 61 and 62 interconnected so that the output of each gate is applied to one input of the other gate. The remaining inputs of the NOR gates form the S and R inputs of the flip-flop circuit, in a manner well known to the art. The $\bar{Q}$ output of gate 60 is applied to an output circuit 64 formed by the series combination of a P-channel transistor 65 and an N-channel transistor 66 to produce the clock output at a terminal 67.

A second reference level is established by a P-channel transistor 70 and an N-channel transistor 71, which are connected between $+V_{bb}$ and $-V_{bb}$. The control electrode of transistor 70 is connected to $C_t$, so that upon the capacitor voltage discharging to a level above the threshold level of the devices, the devices conduct and an output signal is produced. This is applied to the SET input of flip-flop 60 by a control line 72. An N-channel transistor 73, connected to an on-off control line 52 through an inverter 74, also supplies a SET signal to flip-flop 60 when the oscillator is in the OFF state. P and N-channel transistors 76 and 77 form an inverter 79, and P and N-channel transistors 75 and 76 will limit cross-over current through the inverter. An N-channel transistor 80, also connected to inverter 74, allows the SET mode of flip-flop 60 when the clock circuit is switched off.

The gates of transistors 31 and 35 are each connected to the clock output terminal 67 by line 36 and are thereby biased on and off by the clock output pulses. When connected as shown, a HIGH clock output pulse will bias transistor 31 on while biasing transistor 35 off. Similarly, a LOW clock output pulse will bias transistor 31 off while biasing transistor 35 on. It will be noted that with this arrangement simultaneous actuation of the timing capacitor charge and discharge cycles is precluded.

Assuming the clock output is a logic HIGH, N-channel transistor 31 will be biased on, thereby providing a charge path for timing capacitor $C_t$ through transistors 31, 32 and 33. The timing capacitor charge current $i_{cc}$ is determined by the gain ratio between transistors 32 and 43, and in this embodiment is set at 25 times the current $i_{43}$) through transistor 43 of the Wilson current source 40. The discharge current $i_{cd}$ is determined by the gain ratio between transistors 34 and 42, and in this embodiment is set to $7.5 \times i_{42}$ where $i_{42}$ is the current through transistor 42.

In operation, suitable operating voltages are applied to the circuit at $+V_{bb}$ and $-V_{bb}$. The clock circuit is conditioned to an "ON" state through application of a logic-HIGH signal at ON/OFF terminal 51. The logic-HIGH signal at terminal 51 biases an N-channel transistor 81 on, resulting in the application of $-V_{bb}$ to the Wilson current source 40. The logic HIGH signal also serves to bias on transistor 33, which in turn enables the timing capacitor charge circuit formed by transistors 31, 32 and 33.

As timing capacitor $C_t$ is charged through the capacitor charge circuit, the capacitor becomes more and more negative with respect to $+V_{bb}$. Upon the capacitor reaching a sufficiently negative level, P-channel transistors 55 and 56 are biased on. This results in a logic HIGH signal being applied to the reset terminal R of RS flip-flop 60, causing the clock output to become logic LOW. The logic LOW clock output, when applied to the gates of transistors 31 and 35, biases transistor 31 off to terminate the timing capacitor charge period, and biases transistor 35 to initiate the discharge period.

As capacitor $C_t$ discharges, it becomes decreasingly negative with respect to $+V_{bb}$. When the potential across the capacitors reaches 0.8 V, P-channel transistor 70 is biased off, resulting in a logic LOW signal being applied to the S set terminal of flip-flop 60, thereby causing the clock output to once again become logic HIGH and the charging cycle to begin anew.

The clock frequency is determined by the relative levels of charge and discharge current applied to and drawn from timing capacitor $C_t$, and the threshold voltages established by P-channel transistors 55, 56 and 70. During the charge period, capacitor $C_t$ is charged until the threshold voltage of P-channel transistor 56 is reached. The time required for this to happen is a function of the capacitor charge current $i_{cc}$, the threshold voltage, and the capacitance value of $C_t$. An increase in capacitor charge current will result in a decrease in the time required for the capacitor to charge to the threshold voltage established by transistor 56, while decreasing the threshold voltage (with respect to $-V_{bb}$) will increase the time required for the capacitor to charge to that voltage. Similarly, increasing the discharge current $i_{cd}$ through transistors 34 and 35 will result in a decrease in the time necessary for the timing capacitor voltage to reach the threshold voltage of transistor 70. Consequently, it is seen that increasing either or both the charge and discharge currents will result in a shorter clock period and thus a higher clock output frequency. The charge and discharge curents may be increased or decreased by adjusting the resistance of variable resistor 47 to vary the output of Wilson current source 40. Thus, by adjusting resistor 45, the output frequency of the clock circuit may be adjustable over a predetermined frequency range, which in this embodiment, may extend from 8 kHz to 320 kHz.

Figure 4:
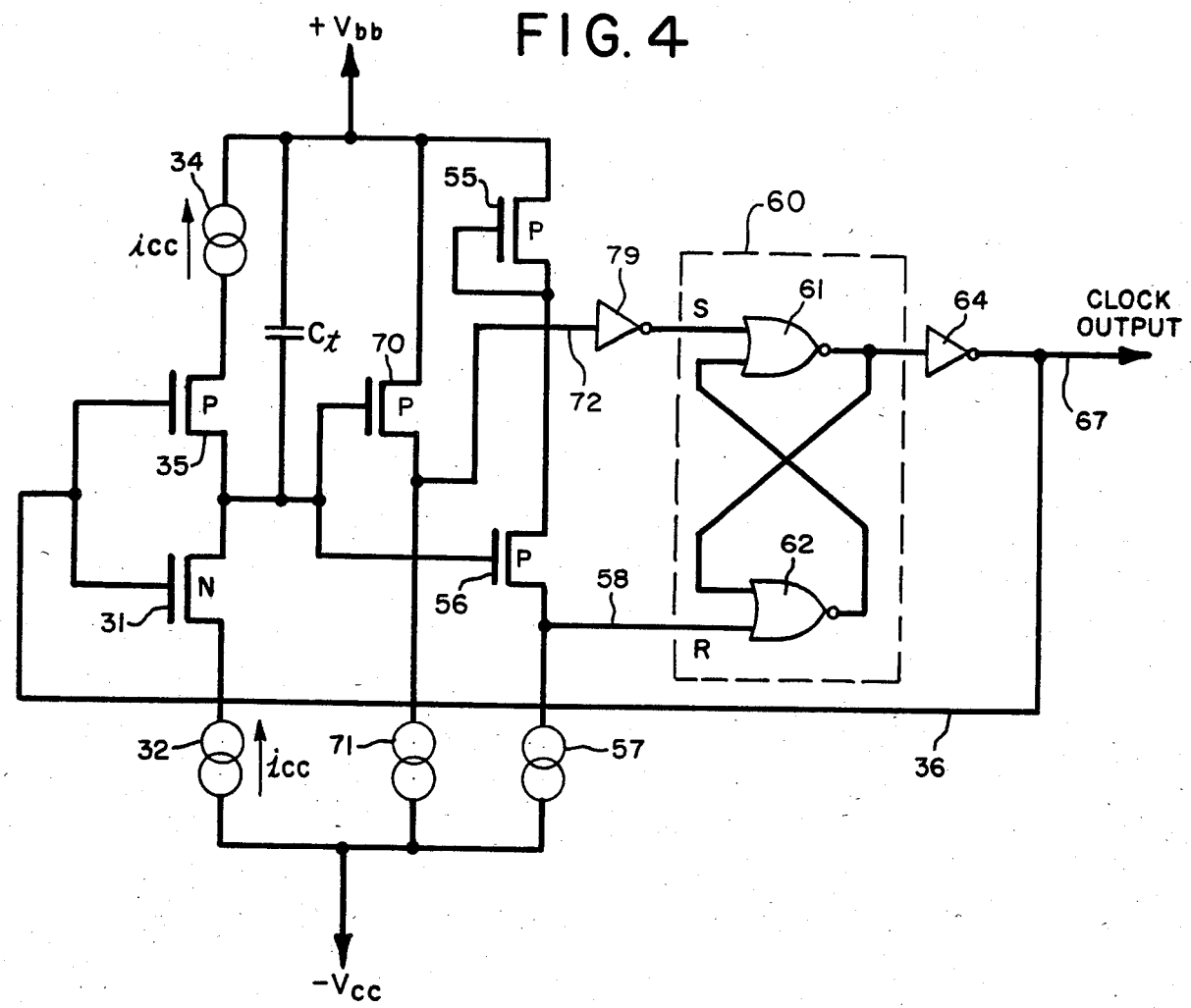
FIG. 4 is a simplified schematic diagram of the clock circuit of FIG. 3 showing the principal elements thereof.

The operation of the clock circuit may be more readily understood by reference to the simplified schematic diagram of FIG. 4. A charge circuit path for timing capacitor $C_t$ is provided by transistor 31 and transistor 32, which may be taken as a constant current source by reason of its association with Wilson current source 40. A discharge circuit is formed by transistors 34 and 35, the former being taken as a constant current source by reason of its association with current source 40. Whether capacitor $C_t$ is charging or discharging is determined by which of transistors 31 and 35 is biased on at the time. A logic HIGH at the clock output terminal 67 results in transistor 31 being biased on and transistor 35 being biased off to accomplish the capacitor charge period. A logic LOW at the clock output biases transistor 31 off and transistor 35 on, thereby terminating the charge period and accomplishing the discharge period. Since the charge and discharge currents are each held constant by reason of constant current sources 32 and 34, the time required to charge and discharge the capacitor between fixed voltage levels remains constant.

The voltage levels between which the voltage across the timing capacitor varies are determined by transistors 55, 56 and 57. A first threshold voltage is established by the combined gate to source voltages ($V_{gs}$) of transistors 55 and 56. Current through these transistors is maintained constant by means of transistor 57, which is a constant current source by reason of its association with the Wilson current source and serves as a pull down active load. Maintaining constant current through transistors 55 and 56 stabilizes the $V_{gs}$ of the transistors, thereby improving the stability of the threshold voltage they establish. A second threshold voltage is established by transistor 70. Transistor 71, which serves as a pull down active load by reflecting the current flowing through the Wilson current source, maintains a LOW logic state at line 72 when transistor 70 is in the off state.

When the timing capacitor voltage reaches the first threshold level of transistors 55 and 56, they become biased on causing a logic-high signal to be applied to the reset terminal R of flip-flop 60. This results in the clock output 67 becoming logic LOW. The logic LOW clock output signal thus provided biases transistor 31 off, thereby interrupting charge current to the timing capacitor. The signal also biases transistor 35 on, thereby allowing the capacitor to discharge through transistor 35 at a current level determined by transistor constant current source 35.

As the capacitor voltage drops by reason of the capacitor being discharged, the gate voltage of transistor 70 is reduced until its cutoff threshold voltage is reached. At that time, transistor 70 is biased off, causing a logic LOW signal to be applied to the input of inverter 79, and a logic HIGH signal to be applied to the set input of flip-flop 60. This results in the clock output 67 becoming logic HIGH. A HIGH signal at the clock output biases transistor 35 off, thereby ending the discharge cycle, and biases transistor 31 on, thereby allowing the timing capacitor to charge through transistor 31 at the desired charge current $i_{cc}$. As the capacitor charges, the voltage applied to the gate electrodes of transistors 56 and 70 becomes increasingly negative until the first threshold voltage is once again reached, whereupon the timing cycle begins anew.

In order to achieve frequency stability, it is necessary that both the charge and discharge periods of the timing capacitor be maintained constant. The factors which may influence the frequency stability of the clock circuit are changes in ambient temperature, and changes in the supply voltage as the battery ages.

Although the Wilson current source 40 employed in the clock circuit described herein is virtually voltage-independent, it is temperature sensitive because electron mobility increases at higher temperatures. Therefore, an increase in temperature causes the reference current provided by the Wilson current source to increase. Such an increase results in a higher charging current $i_{cc}$, and hence in less time being required to charge the timing capacitor $C_t$ to a given voltage. Similarly, discharge current $i_{cd}$ is increased and the capacitor discharges from a given voltage more quickly. Consequently, the charge and discharge periods of the timing capacitor are decreased and the clock output frequency is increased. Therefore, in order to achieve temperature independence in the clock circuit, it is necessary to compensate for the changes in the reference current provided by the Wilson current source which result from changes in ambient temperaure.

In accordance with the invention, temperature compensation circuitry is provided in the form of the previously mentioned series combination of P-channel transistors 55 and 56. As previously developed, transistors 55 and 56 establish a threshold voltage which, when reached by capacitor $C_t$ causes a transition from the charge to the discharge cycle. Since the charge and discharge periods are determined by a combination of both capacitor rate of charge/discharge and threshold voltage, it is seen that, for given charge and discharge currents, a change in the threshold voltage established by transistors 55 and 56 results in a corresponding change in the timing capacitor charge and discharge periods. Consequently, by varying the threshold voltage with changes in temperature, it is possible to compensate for temperature-induced variations in the rate of charging current and maintain a desired output frequency.

The threshold voltage at transistor 55 and 56 is established by two factors; (1) the sum of $V_{gs}$ of transistors 55 and 56 and (2) the load applied to those transistors by active load transistor 57. Since transistor 57 is a current mirror of transistors 43 and 44, any changes in the current flowing through the Wilson current source 40 will change the loading effect of transistor 57. As mentioned before, an increase in temperature will cause an increase in the current flowing through the Wilson current source 40 which will increase the rate of charge and discharge of $C_t$. This, if left uncompensated, will increase the oscillator frequency in proportion to temperature increases. However, loading transistor 57 also responds to current increases in the Wilson current source 40 by increasing its load to transistors 55 and 56. The net result is that capacitor $C_t$ must charge to a more negative voltage in order for transistors 55 and 56 to overcome the higher pull down effect of transistor 57. Therefore, the frequency of the clock will be rendered independent of temperature changes.

Figure 5:
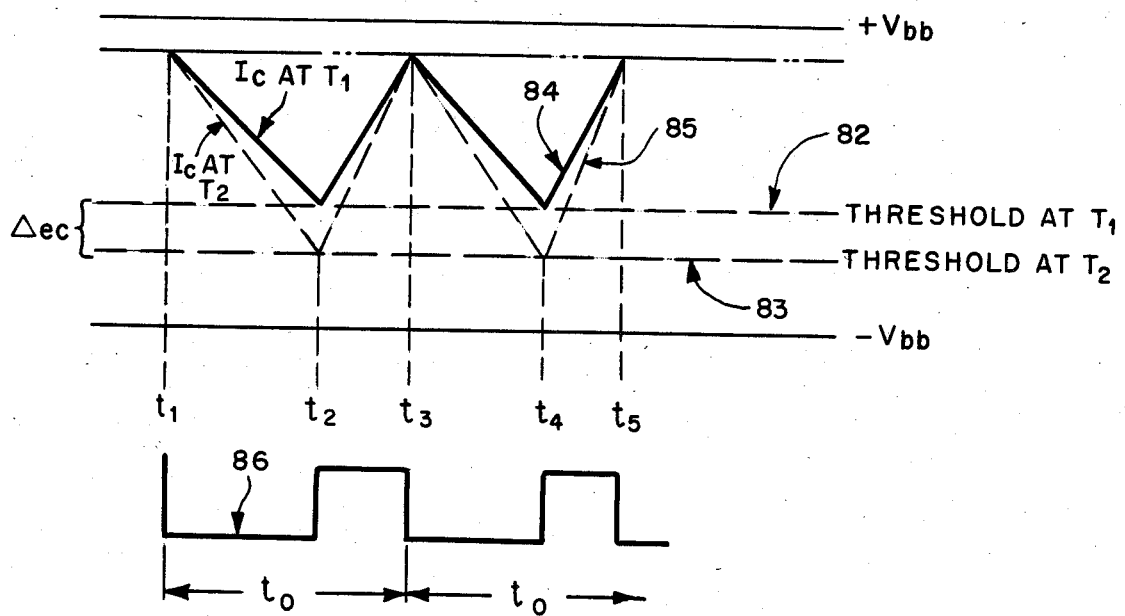
FIG. 5 is a graphical representation of voltage waveforms taken at various points of the clock circuit shown in FIG. 4, useful in understanding the operation thereof.

The operation of the temperature compensation circuitry may be more readily understood by reference to FIG. 5, which depicts the capacitor voltage waveforms at two different temperatures $T_1$ and $T_2$, and the corresponding clock circuit output waveform. The threshold established by transistors 55 and 56 at temperatures $T_1$ and $T_2$ are as indicated by lines 82 and 83, respectively, and the voltage across capacitor $C_t$ at temperatures $T_1$ and $T_2$ is indicated by lines 84 and 85, respectively. Because the current supplied by the Wilson source current is greater at temperature $T_2$ than at temperature $T_1$, the rate of charge and discharge is greater at temperature $T_2$ than it is at temperature $T_1$. Consequently, the slope of the capacitor voltage waveform 85 during the charge cycle is greater at temperature $T_2$ than the slope of the charge waveform 84 at temperature $T_1$. Furthermore, after a given period of time (such as time interval $t_1-t_2$), and assuming a common starting time and voltage, the timing capacitor will charge to a higher voltage when the capacitor current is higher than it will when the capacitor current is reduced.

The clock output 86 is seen to alternate between logic HIGH and logic LOW. While the timing capacitor is being charged, the clock output is constant at logic high. During the capacitor discharge period ($t_2-t_3$, FIG. 5) the clock output is constant logic low. In operation, the timing capacitor is charged during the charge periods $t_1-t_2$, and $t_3-t_4$, and discharged during the discharge periods $t_2-t_3$, and $t_4-t_5$. The total period for one clock pulse is designated $t_0$ and comprises one complete charge/discharge period. As long as the capacitor charge periods ($t_1-t_2$, and $t_3-t_4$) and discharge periods ($t_2-t_3$, and $t_4-t_5$) remain constant, the clock period $t_0$ will remain constant, and the clock output frequency will be stable.

As provided by the invention, the charge and discharge periods are maintained constant with temperature change by adjusting the threshold voltage so that a higher voltage threshold exists at higher temperatures. At temperature $T_1$, the capacitor voltage 84, reaches the $T_1$ threshold level at time $t_2$. At temperature $T_2$, the capacitor voltage exceeds the capacitor voltage at temperature $T_1$ by $\Delta e_c$, the difference between the threshold voltage at $T_2$ and the threshold voltage at $T_1$. Consequently, the gain ratio between transistors 43 and 71 and 43 and 57 are selected so that the difference between the threshold voltages at temperatures $T_2$ and $T_1$ equals the difference in capacitor charge rate existing at $t_2$ by reason of the increased current sourcing current at temperature $T_2$. When the components are properly selected, the transition from the charge to discharge cycles will occur after precisely the same time period and will do so independently of any change in ambient temperature.

In further accord with the invention, clock circuit 28 includes separate charge and discharge circuits for the timing capacitor $C_t$. Since the charge and discharge circuits operate independently of each another, the charge and discharge currents need not be equal, and can selected for most efficient operation of the clock circuit. For given current references at transistors 44 and 42 of Wilson current source 40, the charge current is set by the current gain ratio between transistors 32 and 40, and the discharge current is set by the current gain ratio between transistors 34 and 42. In the present embodiment, for example, gain ratio between transistors 44 and 32 is 1:25 and the gain ratio between transistors 42 and 34 is 1:7.5, resulting in a charge current which is approximately 3.33 times the discharge current. Consequently, during approximately 23% of the cycle the capacitor is being charged, while during approximately 77% of the cycle the capacitor is being discharged. Thus, battery current is drawn only during the charge cycle, while in a typical regenerative oscillator charge current is drawn during the entire cycle. A further saving in power is obtained by charging capacitor $C_t$ between the threshold established by P-channel transistor 70, (0.8 V, for example) and the threshold established by transistors 55 and 56 (3.0 V, for example). Then, for a battery voltage of 3.6 V for example, the capacitor voltage varies over a range of 2.2 V. In comparison, a typical regenerative oscillator the capacitor voltage would vary to the extend of the battery voltage. It will be appreciated that by selecting various current gain characteristics for the active devices of clock circuit 28, it is possible to select different clock duty cycles to accommodate particular applications.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A clock circuit for use in a battery operated cardiac pacer or the like, comprising:
   a timing capacitor;
   charage circuit means operable in response to an applied bistable logic control signal for applying a charge current to said timing capacitor when said control signal is of one logic state;
   discharge circuit means operable in response to said applied logic control signal for applying a discharge current to said timing capacitor when said control signal is of opposite logic state;
   at least one of said circuit means producing a current undesirably varying as a function of ambient temperature;
   first threshold means responsive to the voltage level across said timing capacitor for setting said logic control signal to said one logic state to inhibit said discharge circuit means and actuate said charge circuit means upon said capacitor voltage reaching a first threshold voltage;
   second threshold means responsive to the voltage level across said timing capacitor for setting said logic control signal to said opposite logic state to inhibit said charge circuit means and actuate said discharge circuit means upon said capacitor voltage reaching a second threshold voltage; and
   temperature compensating means in circuit relationship with at least one of said threshold means for varying the threshold voltage thereof in response to changes in temperature whereby the frequency remains substantially constant notwithstanding changes in ambient temperature.

2. A clock circuit as defined in claim 1 wherein said charge and discharge circuit means include a constant current source.

3. A clock circuit as defined in claim 2 wherein said constant current source current varies as a function of temperature.

4. A clock circuit as defined in claim 3 wherein said first threshold voltage increases in proportion to temperature induced increases in said constant current source current and decreases in proportion to temperature induced decreases in said constant current source current.

5. A clock circuit as defined in claim 1 wherein said temperature compensating means include a MOS transistor acting as a temperature-dependent active load to another MOS transistor, thereby causing the associated threshold voltage to vary directly in response to temperature induced changes in the rate of charge and discharge of the timing capacitor.

6. A clock circuit comprising:
   a timing capacitor for providing an increasing capacitor voltage in response to being charged by a charge current and providing a decreasing capacitor voltage in response to being discharged by a discharge current;
   capacitor charge circuity having a charge period during which said charge current is provided to said timing capacitor, and having a discharge period during which said discharge current is drawn from said timing capacitor, at least one of said currents being undesirably dependent on ambient temperature, said charge and discharge periods alternately occurring in response to an applied control signal;
   clock control circuity having lower and upper threshold voltages, and responsive to said capacitor voltage, whereby said control signal is provided and applied to said capacitor charge circuitry in response to said capacitor voltage alternately reaching said upper and lower threshold voltages; and
   temperature compensating circuitry for varying at least one of said threshold voltages in response to changes in ambient operating temperature to maintain a substantially constant charge-discharge cycle frequency notwithstanding changes in said ambient operating temperature.

7. A clock circuit as defined in claim 6 wherein said capacitor charge circuit includes a constant current source for providing said charge and discharge curents.

8. A clock circuit as defined in claim 7 wherein the current supplied by said constant current source varies as a function of temperature.

9. A clock circuit as defined in claim 8 wherein said lower threshold voltage varies as a function of temperature so that said upper threshold voltage increases in proportion to temperature induced increases in said constant current source current and decreases in proportion to temperature induced decreases in said constant current source current.

10. A clock circuit as defined in claim 9 wherein said temprature compensating circuitry varies said lower threshold voltage in response to changing temperature so that said charge and discharge periods remain substantially constant over a range of said ambient operating temperatures.

11. A clock circuit as defined in claim 10 wherein said temperature compensating circuitry includes a MOS transistor acting as temperature dependent active load to another MOS transistor, thereby causing said lower threshold voltage to vary in response to temperature induced changes in the rate of charge and discharge of the timing capacitor.

12. A clock circuit as defined in claim 11 wherein all active devices comprise CMOS devices.

13. A clock circuit as defined in claim 6 wherein said timing capacitor charge current is greater than said capacitor discharge current.

* * * * *